(12) United States Patent
Ushikubo et al.

(10) Patent No.: US 6,294,685 B1
(45) Date of Patent: Sep. 25, 2001

(54) METHOD FOR GAS PHASE CATALYTIC OXIDATION OF HYDROCARBON

(75) Inventors: Takashi Ushikubo; Kazunori Oshima, both of Yokohama; Itaru Sawaki, Kurashiki; Ken Shiraga, Yokkaichi; Satoshi Kobayakawa, Yokkaichi; Hideaki Takumi, Yokkaichi, all of (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/462,644

(22) PCT Filed: Jul. 14, 1998

(86) PCT No.: PCT/JP98/03151
  § 371 Date: Feb. 3, 2000
  § 102(e) Date: Feb. 3, 2000

(87) PCT Pub. No.: WO99/03825
  PCT Pub. Date: Jan. 28, 1999

(30) Foreign Application Priority Data

Jul. 14, 1997 (JP) .................................................. 9-188155

(51) Int. Cl.$^7$ .................................................. C07C 255/00
(52) U.S. Cl. .......................................... 558/319; 558/323
(58) Field of Search ...................................... 558/319, 323

(56) References Cited

U.S. PATENT DOCUMENTS

| 5,049,692 | 9/1991 | Hatano et al. | 558/319 |
| 5,231,214 | 7/1993 | Ushikubo et al. | 558/319 |
| 5,281,745 | 1/1994 | Ushikubo et al. | 558/319 |
| 5,422,328 | 6/1995 | Ushikubo et al. | 502/312 |
| 5,472,925 | 12/1995 | Ushikubo et al. | 502/312 |
| 5,534,650 | 7/1996 | Ushikubo et al. | 558/319 |
| 5,750,760 | 5/1998 | Ushikubo et al. | 558/319 |

FOREIGN PATENT DOCUMENTS

| 48-79988 | 10/1973 | (JP) . |
| 57-209641 | 12/1982 | (JP) . |
| 59-193136 | 11/1984 | (JP) . |
| 2-231459 | 9/1990 | (JP) . |
| 7-144132 | 6/1995 | (JP) . |

*Primary Examiner*—Jane C. Oswecki
*Assistant Examiner*—Joseph Murray
(74) *Attorney, Agent, or Firm*—Oblon, Spivak, McClelland, Maier & Neustadt, P.C.

(57) ABSTRACT

A method for a gas phase catalytic oxidation reaction of a hydrocarbon, which comprises: subjecting an alkane having a carbon number ranging from 3 to 8 and/or an alkene having a carbon number ranging from 2 to 8 to a gas phase catalytic oxidation reaction to produce a vapor phase oxidation product in the presence of a mixed metal oxide catalyst, wherein the reacion is conducted in the presence of particles substantially inert to the reaction in an amount within a range of the same amount as the amount of catalyst to 99 wt. % in all particles.

18 Claims, No Drawings

METHOD FOR GAS PHASE CATALYTIC OXIDATION OF HYDROCARBON

CROSS-REFERENCE TO RELATED APPLICATIONS

The present application is a nonprovisional application having Ser. No. 09/462,644 filed Feb. 3, 2000 which is a 371 of PCT/JP98/03151 filed Jul. 14, 1998.

BACKGROUND OF THE INVENTION

1. Technical Field

The present invention relates to an improved method for a gas phase catalytic oxidation reaction of a hydrocarbon. Specifically, it relates to a method for producing an $\alpha$, $\beta$-unsaturated nitrile (hereinafter referred to as a nitrile) and/or an unsaturated carboxylic acid by subjecting an alkane having a carbon number of from 3 to 8 and/or an alkene having a carbon number of from 2 to 8 to a gas phase catalytic oxidation reaction in the presence of ammonia. Particularly, it relates to an improved method for producing a nitrile using an alkane having a carbon number of from 3 to 8 as a raw material.

2. Background Art

A gas phase catalytic reaction of an alkane having a carbon number of from 3 to 8 and/or an alkene having a carbon number of from 2 to 8, is known as a method for thereby producing an unsaturated carboxylic acid such as acrylic acid, or as a method for producing a nitrile such as acrylonitrile or methacrylonitrile by the reaction in the presence of ammonia. Particularly, acrylonitrile and methacrylonitrile are widely utilized as important raw materials for preparing fibers, synthetic resins, synthetic rubbers, etc., and they are produced on an industrial scale. As a method for producing these nitriles, an ammoxidation method has heretofore been employed as the most common method, wherein an olefin such as propylene or isobutene is subjected to a gas phase catalytic reaction at a high temperature with ammonia and oxygen in the presence of a suitable catalyst.

On the other hand, recently, an interest has been drawn to a method for producing acrylonitrile and methacrylonitrile by an ammoxidation reaction method wherein a lower alkane such as propane or isobutane is used as a starting material instead of an olefin, for an economical reason such as the difference in price between propane and propylene or a difference in price between isobutane and isobutene, and researches and developments of catalysts suitable for such a reaction, have been carried out and various reports have been made. As examples of such reports, a Mo—Bi—P—O type catalyst (JP-A-48-16887), a V—Sb—O type catalyst (JP-A-47-33783, JP-B-50-23016), a Sb—Sn—O type catalyst (JP-B-47-14371), a Sb—Sn—O type catalyst (JP-B-50-28940), a V—Sb—W—P—O type catalyst (JP-A-2-95439), a catalyst obtained by mechanically mixing a V—Sb—W—O type oxide and a Bi—Ce—Mo—W—O type oxide (JP-A-64-38051), a Cr—Sb—W—O type catalyst (JP-A-7-157461) and a Mo—Sb—W—O type catalyst (JP-A-7-157462) are, for example, known. Further, the present inventors have also reported on e.g. a Mo—V—Nb—Te—O type catalyst particularly suitable for this method (JP-A-2-257, JP-A-5-208136).

However, in each of the methods using these catalysts, the selectivity for intended nitrites is not necessarily adequate, and they are not yet satisfactory as industrial methods. Further, in order to improve the selectivity for nitrites, a method has, for example, been proposed wherein a small amount of an organic halide, an inorganic halide or a sulfur compound, is added to the reaction system, but such a method has a problem such as corrosion of the reaction apparatus or complication in the purification of the formed nitrites, and each method has a practical difficulty in industrial application.

The present inventors have studied the characteristics of this reaction in detail in order to improve the selectivity from an alkane to the desired nitrile and as a result, have found it possible to form a nitrile at high selectivity by adjusting the ratio in concentration of alkane:ammonia:oxygen in the reaction gas to be supplied, within a predetermined range, and by suppressing the conversion of the supplied alkane to a level of at most a predetermined value, and they have further found it possible to substantially increase the yield of the nitrile from the alkane by separating the nitrile in an efflux from the reactor and supplying a recovered gas containing an unreacted alkane again into the reactor, and have previously proposed (JP-8-255338).

Further, the present inventors have studied a method for producing nitrites efficiently by one of the above-mentioned methods, or by a combination of a plurality of such methods, or by replacing such methods, and they have found it possible to effectively control the reaction temperature and the quantity of heat generated by the reaction, by the presence in the reactor of a predetermined amount of particles inert to the reaction other than the catalyst particles, whereby nitrites can more effectively be produced, and thus have arrived at the present invention.

Further, the present invention has been accomplished on the basis of a discovery that this method provides the same effects also in a gas phase catalytic oxidation reaction in a fluidized bed reactor of not only an alkane having a carbon number of from 3 to 8 but also an alkene having a carbon number of from 2 to 8.

Further, in the present invention, it is proposed to withdraw the mixed metal oxide catalyst used for the reaction in the form of a mixture with the particles inert to the reaction and to separate and recover the inert particles from the mixture, and an extensive study has been carried out on a method for such separation and recovery, whereby it has been found it possible to accomplish the above object by permitting the inert particles to be present again in the reactor.

DISCLOSURE OF THE INVENTION

The gist of the present invention relates to a method for a gas phase catalytic oxidation reaction of a hydrocarbon, which comprises subjecting an alkane having a carbon number of from 3 to 8 and/or an alkene having a carbon number of from 2 to 8 to a gas phase catalytic oxidation reaction in the presence of a mixed metal oxide catalyst, wherein the reaction is carried out in the presence in the reactor of particles substantially inert to the reaction in an amount within a range of from the same amount as the amount of the catalyst to 99 wt % in all particles in the reactor. The present invention is particularly suitable for a method for a gas phase catalytic oxidation reaction of an alkane having a carbon number of from 3 to 8.

Further, the present invention is suitable particularly for a method for producing an $\alpha$, $\beta$-unsaturated nitrile by a so-called ammoxidation reaction wherein the gas phase catalytic oxidation reaction is carried out in the presence of ammonia.

Still further, the present invention resides in a method for a gas phase catalytic oxidation reaction of a hydrocarbon, wherein the mixed metal oxide catalyst used for the reaction, is withdrawn in the form of a mixture with the inert particles, and the mixed metal oxide catalyst and the inert particles are separated and recovered from the mixture.

BEST MODE FOR CARRYING OUT THE INVENTION

Now, the present invention will be described in detail.

The method for a reaction of the present invention is preferably applied to a gas phase catalytic reaction wherein an alkane having a carbon number of from 3 to 8, such as propane, butane, isobutane, pentane, hexane, heptane or octane, preferably propane and/or isobutane, or an alkene having a carbon number of from 2 to 8, such as ethylene, propylene or isobutylene, is used as a raw material. Specifically, it may, for example, be production of acrolein and/or acrylic acid from propane, production of methacrolein and/or methacrylic acid from isobutane, production of maleic anhydride from n-butane, production of ethylene and/or acetic acid from ethane, production of acrolein and/or acrylic acid from propylene, production of acrylonitrile from propylene, production of methacrolein and/or methacrylic acid from isobutylene, or production of dichloroethane from ethylene.

Further, the present invention is suitable for a method for producing an $\alpha$, $\beta$-unsaturated nitrile by so-called ammoxidation reaction wherein the gas phase catalytic oxidation reaction is carried out in the presence of ammonia. Particularly, it is suitable for a method for a gas phase catalytic reaction of an alkane having a carbon number of from 3 to 8, such as production of a nitrile from propane, butane, isobutane, pentane, hexane or heptane, or production of acrylonitrile from propane, or methacrylonitrile from isobutane.

Further, in some cases, it is applicable also to combined production of a nitrile and an unsaturated carboxylic acid, specifically acrylonitrile and acrylic acid from propane.

Or, it is also applicable to production from a mixture of an alkane and an alkene, of their nitrites, unsaturated carboxylic acids or acid anhydrides.

In the present invention, it is necessary that at the time of such a gas phase catalytic oxidation reaction, in addition to the mixed metal oxide catalyst, particles substantially inert to the reaction are present in a predetermined amount.

Namely, for example, in a case where a nitrile is obtained from an alkane by a gas phase catalytic oxidation reaction, as the amount of the nitrile produced per the unit catalyst amount and per unit time increases, the quantity of heat formed during the reaction increases, whereby it has been difficult to sufficiently remove the reaction heat by a conventional reaction system, and it becomes difficult to control the reaction temperature. For such a control, improvements in the structure of the reactor and improvements of e.g. a cooler for removing the heat, mounted on the reactor, are being made, but such attempts have a drawback such that installation of the apparatus tends to be expensive, or the operation tends to be complex.

Further, with respect to the quantity of heat generated per catalyst particles, if the quantity of the heat generated increases, the temperature of the catalyst particles tends to be abnormally high, and the active structure whereby the catalyst effectively acts, tends to be hardly maintained, whereby a decrease in the catalytic performance tends to be observed.

Further, with respect to the reaction system, a fluidized bed reaction system is preferably employed, since the control of the reaction temperature or the reaction heat is thereby easy, but in such a case, the amount of catalyst particles tends to be inadequate to attain a sufficiently high fluidized bed height, and it becomes difficult to carry out the fluidized bed reaction smoothly.

Here, the present inventors have found that by the presence of particles substantially inert to the reaction in the reactor in an amount of at least the same amount as the amount of the catalyst, it is possible to effectively remove the heat formed during the reaction by thermal conduction from the catalyst to the inert particles, and especially when a fluidized bed reaction system is employed, it is possible to accomplish the desired fluidized bed height and thereby to facilitate the control of the reaction. Further, the upper limit of the amount of the inert particles is at most 99 wt % in all particles in the reactor taking it into consideration that the catalyst is indispensable for the reaction. Especially when the practicality is taken into consideration, the amount of the inert particles is preferably within a range of at least 60 wt % and at most 95 wt % in all particles in the reactor.

Specifically, as such particles substantially inert to the reaction, it is preferred to employ an oxide containing at least one element among Si, Al, Ge, Ga, Zr, Ti, Mo, W, Cr, Nb, Ta, Fe, Co, Ni, an alkaline earth metal and a rare earth element, since it is thereby possible to maintain the selectivity for the desired product such as a nitrile at a high level.

As such particles, commercially available oxides may be used as they are, or they may be produced by a conventional method by using a raw material of the desired metal oxide, and they may be adjusted into a desired shape or size for use, as the case requires. For example, when silica is used, a commercially available powdery or spherical silica may be employed, or one produced by subjecting a silica sol or a silicon halide or alkoxide by itself or in the form of a solution, to heat treatment, may be employed.

The oxide particles may be subjected to heat treatment as the case requires. As a condition for this heat treatment, a temperature range of at least 300° C., preferably from 500 to 1,500° C., may be mentioned, and the atmosphere and the treating method, time, etc., are not particularly limited, but the treatment is preferably carried out under conditions of from 1 minute to 10 hours in air, or in an inert gas such as nitrogen, argon or helium or in vacuum. Further, in some cases, it is preferred to carry out the heat treatment by an addition of a small amount of a compound containing boron to such oxide particles, whereby the particles tend to be more inert to the reaction.

Further, the effect of the present invention is such that the efficiency differs also depending upon the catalyst to be used. However, so long as it is a catalyst useful for a gas phase catalytic oxidation reaction of an alkane or alkene, even if a certain difference may exists depending upon the type of the catalyst, it is possible to control the reaction temperature or the reaction heat and to carry out the reaction efficiently by the method of the present invention.

A mixed metal oxide catalyst with which the method of the present invention is particularly effective, is one containing a mixed metal oxide which comprises molybdenum, vanadium, X, Y and oxygen (X is at least one member among tellurium and antimony, and Y is at least one element selected from the group consisting of niobium, tantalum, tungsten, titanium, aluminum, zirconium, chromium, manganese, iron, ruthenium, cobalt, rhodium, nickel, palladium, platinum, bismuth, boron, indium, phosphorus, a rare earth element, an alkali metal and an alkaline earth metal) as essential components, and wherein the proportions of the above essential components except for oxygen satisfy the following conditions:

$$0.25 < rMo < 0.98$$
$$0.003 < rV < 0.5$$
$$0.003 < rX < 0.5$$
$$0.003 < rY < 0.5$$

(wherein rMo, rV, rX and rY are molar fractions of Mo, V, X and Y, based on the total amount of the above essential components except for oxygen), and in the present invention, it is preferred to use such a catalyst.

Particularly preferred is a case wherein Y is at least one member among Nb, Ta, Ti and Bi.

The method for preparation of such a mixed metal oxide catalyst is not particularly limited. For example, a method may be mentioned wherein a solution or an aqueous solution of slurry state containing various raw material components for the mixed metal oxide, is prepared, followed by drying and calcining.

For example, a mixed metal oxide containing molybdenum, vanadium, tellurium and niobium, can be obtained by sequentially adding an aqueous solution of telluric acid, an aqueous solution of ammonium niobium oxalate and an aqueous solution of ammonium paramolybdate to an aqueous solution of ammonium metavanadate in such a ratio that the atomic ratios of the respective metal elements would be predetermined proportions, followed by drying by an evaporation to dryness method, a spray drying method, a freeze drying method or a vacuum drying method, to obtain a dried product, and then, calcining the dried product.

The calcining method may optionally be employed depending upon the nature or volume of the dried product. Usually, heat treatment on an evaporating dish or heat treatment by means of a heating furnace such as a rotary furnace or a fluidized bed furnace, may be applied. The calcining conditions are such that the temperature is usually within a range of from 200 to 700° C., preferably from 250 to 650° C., and the time is usually within a range of from 0.5 to 30 hours, preferably from 1 to 10 hours. Further, calcination may be carried out in an oxygen atmosphere, but it is preferably carried out in the absence of oxygen. Specifically, it is preferably carried out in vacuum or in an atmosphere of an inert gas such as nitrogen, argon or helium.

The mixed metal oxide obtained as described above, may be used by itself as the oxidation catalyst for the present invention. However, in some cases, it is possible to use one having a solution containing an element selected from the group consisting of tungsten, molybdenum, chromium, zirconium, titanium, niobium, tantalum, vanadium, boron, bismuth, tellurium, palladium, cobalt, nickel, iron, phosphorus, silicone, a rare earth element, an alkali metal and an alkaline earth metal, impregnated to such a mixed metal oxide, in order to improve the surface activity of the catalyst.

Further, the above described mixed metal oxide catalyst may be used alone, but may be used in the form of a mixture containing from 1 to 90 wt % of a well known carrier component such as silica, alumina, titania, zirconia, aluminosilicate or diatomaceous earth. Here, such a carrier may be added at any stage such as at the time of preparing the mixed metal oxide or prior to or after the impregnation treatment after the preparation.

This mixed metal oxide catalyst is superior in the yield and selectivity for nitrites, as compared with usual conventional catalysts used for preparation of nitrites from alkanes, whereby preparation of nitrites can be carried out even by a conventional reaction system having a high conversion. However, the efficiency for production of nitrites may be further improved by carrying out the production by maintaining the alkane concentration and/or the compositional ratio of components in the reaction gas within a certain specific range and further adjusting the conversion of the alkane to a level of at least a certain specific ratio, at the time of using this mixed metal oxide catalyst.

Namely, in the present invention, when the reaction is carried out under such conditions that the composition of the reaction gas to be supplied to the reactor particularly in the case of producing a nitrile from an alkane, is made to be alkane:ammonia:oxygen:diluting gas= 1:0.001–0.9:0.1–1.8:0–9 (molar fractions), that the alkane content in the gas is adjusted to be from 10 to 90 vol% and further that the conversion of the alkane is at most 70%, preferably at most 50%, the selectivity of the reaction for the intended nitrile will improve, which will be more advantageous.

Here, the diluting gas is used for adjusting the oxygen partial pressure or the space velocity and is meant for a gas which is not substantially involved in the gas phase catalytic oxidation reaction, and specifically, it may, for example, be nitrogen, argon, helium, carbon dioxide or steam.

To maintain the conversion of the alkane to a low level of e.g. at most 70%, a reaction condition such as the composition of the reaction gas, the reaction temperature, the reaction pressure or the gas space velocity (SV) may be controlled.

In the present invention, the gas phase catalytic oxidation reaction is carried out usually under atmospheric pressure, but it can also be carried out under a low level of elevated pressure or reduced pressure.

In a case where the above mixed metal oxide catalyst is used, the reaction may be carried out at a temperature lower than the conventional ammoxidation reaction of an alkane, for example, within a temperature range of from 340 to 500° C., particularly preferably from 380 to 470° C. Further, the gas space velocity SV in the gas phase reaction is usually within a range of from 100 to 10,000 $h^{-1}$, preferably from 300 to 2,000 $h^{-1}$.

The reaction system to be employed for the method of the present invention is not particularly limited, and the reaction may be carried out in any one of fixed bed, fluidized bed and mobile bed systems. However, because of the exothermic reaction, a fluidized bed system is most common, as the control of the reaction temperature is thereby easy.

When the method for a reaction of the present invention is carried out in a fluidized bed reactor, as the physical properties of the inert particles, the shape is preferably spherical, and the weight average particle size (diameter) is usually within a range of at least 10 $\mu$m and at most 200 $\mu$m, preferably at least 25 $\mu$m and at most 150 $\mu$m. This particle size is not particularly limited, but in many cases, it is preferred that fine particles of at most 10 $\mu$m are not contained. Accordingly, it is preferred to use particles from which particles having sizes smaller than the above range have been removed preferably by a means such as sieving. Further, it is preferred that particles which are too large, are also removed by e.g. sieving, or brought into the above range by e.g. pulverization.

Further, the bulk density is preferably at least 0.5 and at most 2.0, and the crushing strength is preferably at least 5 MPa and at most 15 MPa.

The method for preparation of the catalyst is not particularly limited, but in the case of a fluidized bed catalyst, a common method for producing a fluidized bed catalyst may be employed. For example, it is common to spray dry a solution or a slurry of raw material and to use the obtained product as it is or to subject it to the heat treatment as mentioned above.

The blend ratio of the catalyst particles and the particles inert to the reaction varies depending upon e.g. the type of the reaction, the reaction system, the reaction conditions, the properties of the catalyst, etc., and it is determined particularly taking into consideration the quantity of heat to be generated. Further, in a case where a fixed bed reactor system is employed, it is more preferred that the ratio of the inert particles is not made to be the same throughout the entire catalyst layer, but this ratio is varied depending upon the amount of reaction, for example, so that it will be inversely proportional to the concentration gradient and the conversion rate of the alkane and/or alkene in the reactor.

Further, in the present invention, it is proposed that after carrying out the reaction, the mixed metal oxide catalyst and the particles inert to the reaction are withdrawn from the reactor as they are mixed, and the mixed metal oxide catalyst and the inert particles are separated and recovered from the mixture. Especially, in the present invention, it is proposed that after recovery of the inert particles, they are used again for the reaction. This reuse is particularly preferred, since it is thereby possible to effectively utilize the inert particles, and it is possible to reduce the cost for obtaining such particles, such being economical, and it is also possible to reduce the amount of particles to be disposed as a waste.

As a method for such separation/recovery/reuse, a method may be mentioned wherein the mixture of the inert fine particles and the catalyst after the reaction, is divided into a mixture portion wherein the ratio of the catalyst component is high and a mixture portion wherein the ratio of the inert component is high, and the portion wherein the inert component is high, is reused for the reaction or further separated.

Particularly preferred is a method wherein the mixed metal oxide catalyst and the particles inert to the reaction are separated and recovered specifically by e.g. sieving, air classification, wet classification or magnetic classification.

Among them, separation by sieving utilizes the difference in the particle sizes, and the air classification or the wet classification utilizes the difference in the inertial force of the particles and in the resistance received from the fluid i.e. utilizes the difference in the particle size and the weight of the particles. The magnetic separation utilizes the difference in the magnetic property of the particles.

Here, in a case where the difference in the particle size is utilized to carry out classification by sieving or air classification to separate the inert particles from the catalyst, it is preferred from the viewpoint of the separability that as between the catalyst particles and the inert particles, the weight ratio of the other particles having sizes of at least the weight average particle size of the larger ones, is adjusted to be at most 40%, and the weight ratio of the other particles having sizes of at most the wave average particle size of the smaller ones, is adjusted to be at most 40%.

Further, in a case where the difference in the bulk density of particles is utilized to carry out classification by e.g. air classification, it is preferred also from the viewpoint of the separability and fluidity that the bulk density of particles of either the particles of the mixed metal oxide catalyst or the inert particles, is adjusted to be at least 1.1 times and at most 4.0 times, further preferably at least 1.2 times and at most 3.5 times, of the bulk density of the other particles. If the difference in the specific gravity is less than 1.5 times, the separability tends to be low, and such tends to hinder reuse of the inert particles. If the difference is larger than 4.0 times, when the reaction is carried out in a fluidized bed, classification within the reaction layer tends to be vigorous, which tends to hinder the fluidity.

Further, the difference in strength of the catalyst and the inert particles can be utilized for separation. Namely, the particles of the mixed metal oxide catalyst and the inert particles are made to have a difference in the crushing strength of at least about 10 MPa, and a mixture of the particles of the mixed metal oxide catalyst and the inert particles withdrawn from the reactor, is subjected to pulverization treatment, so that either one of the particles having a smaller crushing strength is pulverized, and the pulverized product is removed, whereby the particles of the mixed metal oxide catalyst and the inert particles can be separated. Here, taking into consideration the possibility of using the inert particles again as being present in the reactor, it is preferred that the inert particles have a higher crushing strength than the catalyst particles so that when the mixed particles are treated in a pulverizer having the pulverization strength adjusted, only the catalyst is pulverized, and the inert particles can be recovered in a non-pulverized state. Of course, after the pulverization treatment, there will be a difference in the particle size such that the inert particles are large, and the catalyst particles are small, and from the product recovered from the pulverization treatment, the inert particles can be recovered by the above-mentioned sieving or air classification. At that time, the strength of the catalyst is preferably at least 5 MPa and at most 15 MPa, as mentioned above. The strength of the inert particles is preferably at least 20 MPa and at most 1,000 MPa. If it is less than 20 MPa, it tends to be difficult to pulverize only the catalyst. Further, if it is stronger than 1,000 MPa, the wall surface of e.g. the pulverizer, the classifier or the reactor, is likely to be abraded.

Further, it is also possible that a substance which is susceptible to a magnetic field, such as a paramagnetic substance, is added to the component of inert particles, and by applying a magnetic field, the inert particles are separated from the mixed particles with the catalyst.

In the foregoing description, the characteristics of the present invention have been described with reference to a case of a reaction (a so-called ammoxidation reaction) to produce a nitrile by subjecting an alkane to a gas phase catalytic oxidation reaction with ammonia. However, as described above, the present invention is applicable in the same manner as described above also to other gas phase catalytic oxidation reactions of alkanes, specifically for the production of acrolein and/or acrylic acid from propane, the production of methacrolein and/or methacrylic acid from isobutane, the production of maleic anhydride from n-butane or the production of ethylene and/or acetic acid from ethane. The ratio of feed gas in this case where ammonia is absent, is preferably such that alkane and/or alkene:oxygen:diluting gas (molar fractions)=1:0.1–5:0.5–40.

Further, the above mentioned method for obtaining a nitrile by subjecting an alkane to a gas phase catalytic oxidation reaction with ammonia, a method for simultaneously obtaining an unsaturated carboxylic acid in addition to the nitrile, is also included.

Further, it is applicable also to a method for subjecting an alkene having a carbon number of from 2 to 8 to a gas phase catalytic oxidation reaction in a fluidized bed reactor having a mixed metal oxide catalyst. Specifically, the production of acrolein and/or acrylic acid from propylene, the production of acrylonitrile from propylene, the production of methacrolein and/or methacrylic acid from isobutylene or the production of dichloroethane from ethylene, may, for example, be mentioned.

Or, it is also applicable to the production, from a mixture of an alkane and an alkene, of their nitrites, unsaturated carboxylic acids or acid anhydrides.

Further, in the present invention, in the case of producing an unsaturated carboxylic acid or a nitrile, the conversion of the alkane is preferably adjusted to be at most 70%. In such a case, in the desired reaction product, an unreacted alkane and an alkene corresponding to the raw material alkane may sometimes be contained, and they may be separated and recovered and again supplied to the reactor, whereby the total yield of the nitrile relative to this alkane and/or alkene, can be increased, such being desirable.

EXAMPLES

Now, the present invention will be described in further detail with reference to Examples and Reference Examples. However, the present invention is by no means restricted to such Examples.

Further, the conversion (%), the selectivity (%) and the yield (%) in the following Examples, are represented by the following formulae, respectively.

Conversion (%) of alkane=(mols of consumed alkane/mols of supplied alkane)×100

Selectivity (%) for desired nitrile=(mols of formed desired nitrile/mols of consumed alkane)×100

Yield (%) of desired nitrile=(mols of formed desired nitrile/mols of supplied alkane)×100

Reference Example 1

Preparation of Mixed Oxide Catalyst ($Mo_1V_{0.3}Te_{0.23}Nb_{0.12}O_n/SiO_2$ 10 wt %)

A mixed metal oxide having the empirical formula $Mo_1V_{0.3}Te_{0.23}Nb_{0.12}O_n/SiO_2$ 10 wt % was prepared as follows. In 5.68 l of warm water, 1.38 kg of ammonium paramolybdate, 0.275 kg of ammonium metavanadate and 0.413 kg of telluric acid were dissolved to obtain a uniform aqueous solution. Further, 0.658 kg of a silica sol having a silica content of 20 wt % and 0.618 kg of an aqueous ammonium niobium oxalate solution having a niobium concentration of 0.659 mol/kg, were mixed thereto, to obtain a slurry. This slurry was dried to remove the water content. Then, this dried product was subjected to heat treatment at about 300° C. until the ammonia odor was no longer present and then calcined at 600° C. for two hours in a nitrogen stream.

The obtained catalyst was sieved to remove particles having diameters of at most 39 μm. The particle size distribution of this mixed metal oxide catalyst was measured by a laser diffraction-scattering type particle size distribution measuring apparatus (LMS-24, trade name, manufactured by Kabushiki Kaisha Seishin Kigyo), whereby the weight average particle size (diameter) was about 50 μm.

Further, the crushing strength of this catalyst was measured by a compression testing apparatus (Autograph, manufactured by Shimadzu Corporation) and found to be about 40 MPa, and the bulk density measured by a powder property measuring apparatus (Multi Tester MT-1000, trade name, manufactured by Kabushiki Kaisha Seishin Kigyo) was 1.0.

Example 1

The same silica sol as used in the production of the mixed oxide catalyst in Reference Example 1, was dried to remove the water content, and then, the obtained solid was calcined at 1,000° C. for two hours in air and further pulverized to obtain silica particles. The weight average particle size of the silica particles was about 19 μm. Further, the crushing strength was about 200 MPa, and the bulk density was 1.2.

Further, of the catalyst, the weight ratio of particles of at most 19 μm which was the weight average particle size of the silica particles, was 0%, and of the silica particles, the weight ratio of particles of at least 50 μm which was the weight average particle size of the catalyst particles, was 18.45%.

400 mg of the silica thus obtained and 100 mg of the mixed oxide catalyst $Mo_1V_{0.3}Te_{0.23}Nb_{0.12}O_n/SiO_2$ 10 wt %, prepared as described in Reference Example 1, were packed into a fixed bed flow type reactor, and a gas phase catalytic oxidation reaction was carried out at a temperature of 429° C. at a ratio of propane:ammonia:oxygen:nitrogen=1:0.3:0.8:3.2 (propane concentration: 18.9 vol %) so that the amount of propane supplied per unit weight of the total amount of the catalyst and the silica, would be 0.371 kg/kg-catalyst·h. As a result, the conversion of propane was 25.0%, the yield of acrylonitrile was 15.4%, and propylene was formed in a yield of 3.6%. The selectivity for acrylonitrile was 61.6%, and the selectivity for propylene was 14.4%.

Example 2

Commercially available silica (Cariact Q50, manufactured by Fuji Silicia K.K.) was calcined at 1,100° C. for 5 hours in an air stream. The weight average particle size of the silica particles was about 30 μm, and the crushing strength was about 250 MPa.

Further, of the silica particles, the weight ratio of particles of at least 50 μm which was the weight average particle size of the catalyst particles, was 34.73%.

400 mg of such silica particles were mixed with 100 mg of the mixed metal oxide catalyst prepared as described in Reference Example 1, and by means of the same fixed bed flow type reactor as described in Example 1, a gas phase catalytic oxidation reaction was carried out at a reaction temperature of 409° C. at a ratio of propane:ammonia:oxygen:nitrogen=1:0.3:0.8:3.2 (propane concentration: 18.9 vol %) so that the amount of propane supplied per unit weight of the total amount of the catalyst and the silica would be 0.371 kg/kg-catalyst·h. As a result, the conversion of propane was 25.0%, the yield of acrylonitrile was 13.5%, and propylene was formed in a yield of 4.3%. The selectivity for acrylonitrile was 54.0%, and the selectivity for propylene was 17.2%.

Example 3

The mixture of the mixed metal oxide catalyst and the silica particles, used for the reaction in Example 2, was sieved by a JIS standard sieve having an opening of 44 μm, to obtain 159 mg of non-pass product and 341 mg of pass product, as recovered products. The compositions of the recovered products were analyzed by an ICP luminescence method, whereby the non-pass recovered product contained 62 wt % of the catalyst component, and the pass recovered product contained 99.7 wt % of the silica particle component.

To 400 g of the pass recovered product thus separated, 100 mg of the mixed metal oxide catalyst prepared as described in Reference Example 1, was mixed, and in the same manner as in Example 1, by means of a fixed bed flow type reactor, a gas phase catalytic oxidation reaction was carried out at a reaction temperature of 411° C. at a ratio of propane:ammonia:oxygen:nitrogen=1:0.3:0.8:3.2 (propane concentration: 18.9 vol %) so that the amount of propane supplied per unit weight of the total amount of the catalyst and the silica would be 0.371 kg/kg-catalyst·h. As a result, the conversion of propane was 25.0%, the yield of acrylonitrile was 13.4%, and propylene was formed in a yield of 4.3%. The selectivity for acrylonitrile was 53.6%, and the selectivity for propylene was 17.2%.

Example 4

120 g of the mixed metal oxide catalyst prepared in Reference Example 1 and 480 g of the same silica particles as in Example 1, were mixed and packed into a fluidized bed reactor having a cyclone, whereby the internal diameter of the fluidized portion was 52.9 mm, whereupon the temperature in the reactor was increased to about 450° C. by supplying only nitrogen, and a gas phase catalytic oxidation reaction was carried out by supplying a gas mixture in a molar ratio of propane:ammonia:oxygen:nitrogen= 1:0.6:1.6:6.4 from a pipe at the bottom of the reactor while fixing the weight ratio of propane (wwH) supplied to the catalyst at a level of about 0.27 g-propane/g-catalyst·h.

The gas formed by the reaction was analyzed, whereby:

Conversion of propan: 42.5%

Yield of acrylonitrile: 25.7%

Yield of propylene: 5.7%

Selectivity for acrylonitrile: 60.4%

Selectivity for propylene: 13.5%

Comparative Example 1

Under the same reaction conditions as in Example 4, without mixing silica particles, in the presence of only the mixed metal oxide catalyst (120 g), the temperature in the reactor was increased to about 380° C. while supplying only nitrogen, and a mixed gas in a molar ratio of propane:ammonia:oxygen:nitrogen=1:0.6:1.6:6.4 was supplied from a pipe at the bottom of the reactor while fixing the weight ratio (wwH) of propane supplied to the catalyst at a level of about 0.27 g-propane/g-catalyst·g.

After supplying this mixed gas, at the lower portion of the catalyst layer, the temperature rose immediately (within 5 minutes), whereby an overheating breaker (set at 480° C.) installed for temperature control, was actuated, and the heater for the reactor and the supply of the reaction gas were stopped, and it was therefore impossible to continue the reaction.

Comparative Example 2

Under the same reaction conditions as in Example 4, without mixing silica particles, in the presence of only the mixed oxide catalyst (6,000 g), the temperature in the reactor was increased to about 380° C. while supplying only nitrogen, and a mixed gas in a molar ratio of propane:ammonia:oxygen:nitrogen=1:0.6:1.6:6.4 was supplied from a pipe at the bottom of the reactor while fixing the weight ratio (wwH) of propane supplied to the catalyst at a level of about 0.27 g-propane/g-catalyst·h.

After supplying this mixed gas, at the lower portion of the catalyst layer, the temperature rose immediately (within 5 minutes), whereby the overheating breaker (set at 480° C.) installed for temperature control, was actuated, and the heater for the reactor and the supply of the reaction gas were terminated, and it was impossible to continue the reaction.

INDUSTRIAL APPLICABILITY

According to the present invention, it is possible to effectively control the reaction temperature and the amount of heat generated by the reaction in a method for a gas phase-catalytic oxidation reaction of a hydrocarbon, specifically in a method for producing a nitrile and/or an unsaturated carboxylic acid by a gas phase catalytic oxidation reaction of an alkane or an alkene, particularly in a method for producing a nitrile using an alkane having a carbon number of from 2 to 8 as a raw material, especially in a case where a fluidized bed reactor is employed, whereby it is possible to produce a nitrile more efficiently. Further, after the reaction, the catalyst component and the component inert to the reaction are separated, and the inert component is re-used without deterioration of the performance, such being very economical.

What is claimed is:

1. A method for a gas phase catalytic oxidation reaction of a hydrocarbon, which comprises:

subjecting an alkane having a carbon number ranging from 3 to 8 and/or an alkene having a carbon number ranging from 2 to 8 to a gas phase catalytic oxidation reaction to produce a vapor phase oxidation product in the presence of a mixed metal oxide catalyst, wherein the reaction is conducted in the presence of particles substantially inert to the reaction in an amount within a range of the same amount as the amount of catalyst to 99 wt. % in all particles.

2. The method for a gas phase catalytic oxidation reaction of a hydrocarbon according to claim 1, which is a method wherein an alkane having a carbon number of from 3 to 8 is subjected to the gas phase catalytic oxidation reaction.

3. The method for a gas phase catalytic oxidation reaction of a hydrocarbon according to claim 1, wherein the gas phase catalytic oxidation reaction is carried out in the presence of ammonia to produce an α, β-unsaturated nitrile.

4. The method for a gas phase catalytic oxidation reaction of a hydrocarbon according to claim 1, wherein the mixed metal oxide catalyst contains a mixed metal oxide which comprises molybdenum, vanadium, X, Y and oxygen wherein X is at least one member selected from the group consisting of tellurium and antimony, and wherein Y is at least one element selected from the group consisting of niobium, tantalum, tungsten, titanium, aluminum, zirconium, chromium, manganese, iron, ruthenium, cobalt, rhodium, nickel, palladium, platinum, bismuth, boron, iridium, phosphorus, a rare earth element, an alkali metal and an alkaline earth metal as essential components, and wherein the proportions of the above essential components except for oxygen satisfy the following conditions:

$0.25 < rMo < 0.98$ $0.003 < rV < 0.5$ $0.003 < rX < 0.5$ $0.003 < rY < 0.5$ wherein rMo, rV, rX and rY are molar fractions of Mo, V, X and Y, based on the total amount of the above essential components except for oxygen.

5. The method for a gas phase catalytic oxidation reaction of a hydrocarbon according to claim 1, wherein the reaction is conducted in the presence of particles substantially inert to the reaction in an amount within a range from 60 wt. % to 95 wt. % in all particles.

6. The method for a gas phase catalytic oxidation reaction of a hydrocarbon according to claim 1, wherein a gas supplied to the reactor has the following composition:

Alkane and/or alkene:oxygen:diluting gas (molar fractions)=1:0.1–5:0.5–40.

7. The method for a gas phase catalytic oxidation reaction of a hydrocarbon according to claim 3, wherein a gas supplied to the reactor has the following composition, the alkane and/or alkene content in said gas is from 10 to 90 vol %, and the reaction is carried out while adjusting the conversion of the supplied alkane to a level of at most 70%:

Alkane and/or alkene:ammonia:oxygen:diluting gas (molar fractions)=1:0.01–0.9:0.1–1.8:0–9.

8. The method for a gas phase catalytic oxidation reaction of a hydrocarbon according to claim 1, wherein the reactor is a fluidized bed reactor.

9. The method for a gas phase catalytic oxidation reaction of a hydrocarbon according to claim 1, wherein the particles substantially inert to the reaction are of at least one oxide of an element selected from the group consisting of Si, Al, Ge, Ga, Zr, Ti, Mo. W, Cr, Nb, Ta, Fe, Co, Ni, an alkaline earth metal and a rare earth element.

10. The method for a gas phase catalytic oxidation reaction of a hydrocarbon according to claim 1, wherein the particles substantially inert to the reaction are at least one oxide of an element selected from the group consisting of Si, Al, Ge, Ga, Zr, Ti, Mo. W, Cr, Nb, Ta, Fe, Co, Ni, an alkaline earth metal and a rare earth element, subjected to heat treatment at a temperature of at least 300° C.

11. The method for a gas phase catalytic oxidation reaction of a hydrocarbon according to claim 1, wherein the alkane is propane and/or isobutane.

12. The method for a gas phase catalytic oxidation reaction of a hydrocarbon according to claim 1, wherein the alkene is ethylene, propylene or isobutylene.

13. The method for a gas phase catalytic oxidation reaction of a hydrocarbon according to claim 1, wherein the particles substantially inert to the reaction are withdrawn in the form of a mixture with the mixed metal oxide catalyst, and the inert particles are separated and recovered from said mixture.

14. The method for a gas phase catalytic oxidation reaction of a hydrocarbon according to claim 13, wherein the reactor is a fluidized bed reactor, each of the weight average particle sizes of the particles substantially inert to the reaction and particles of the mixed metal oxide catalyst, is at least 10 μm and at most 200 μm, the weight ratio of the other particles having sizes of at least the weight average particle size of the larger ones among the weight average particle sizes of these particles, is adjusted to be at most 40%, and the weight ratio of the other particles having sizes of at most the weight average particle size of the smaller ones, is adjusted to be at most 40%, and both particles are separated by the difference in their particle sizes.

15. The method for a gas phase catalytic oxidation reaction of a hydrocarbon according to claim 13, wherein the bulk density of particles of either one of the particles of the mixed metal oxide catalyst and the inert particles, is adjusted to be at least 1.5 times and at most 4.0 times of the bulk density of the other particles, and both particles are separated by the difference in their specific gravities.

16. The method for a gas phase catalytic oxidation reaction of a hydrocarbon according to claim 13, wherein the particles of the mixed metal oxide catalyst and the inert particles have a difference in the crushing strength of at least about 10 MPa, and a mixture of the particles of the mixed metal oxide catalyst and the inert particles withdrawn from the reactor, is subjected to pulverization treatment, so that either one of the particles having a small crushing strength is pulverized, and the pulverized product is removed, whereby the particles of the mixed metal oxide catalyst and the inert particles are separated.

17. The method for a gas phase catalytic oxidation reaction of a hydrocarbon according to claim 13, wherein after the particles of the mixed metal oxide catalyst and the inert particles are separated, said inert particles are used again as being present in the reactor.

18. A method for a gas phase catalytic oxidation reaction of a hydrocarbon, which comprises:

subjecting an alkane having a carbon number ranging from 3 to 8 and/or an alkene having a carbon number ranging from 2 to 8 to a gas phase catalytic oxidation reaction to produce a vapor phase oxidation product in the presence of a mixed metal oxide catalyst, wherein the reaction is conducted in the presence of particles substantially inert to the reaction in an amount within a range of the same amount as the amount of the catalyst to 99 wt. % in all particles while the temperature of the reaction is controlled.

* * * * *